(12) United States Patent
Takahashi et al.

(10) Patent No.: US 10,701,957 B2
(45) Date of Patent: *Jul. 7, 2020

(54) METHOD FOR PRODUCTION OF CAROTENOID

(75) Inventors: Toshiyuki Takahashi, Kanagawa (JP);
Shotaro Uchizawa, Kanagawa (JP);
Hideyuki Dohi, Kanagawa (JP);
Kentaro Shimizu, Tokyo (JP);
Tomoyuki Ishizaki, Tokyo (JP)

(73) Assignee: JXTG NIPPON OIL & ENERGY CORPORATION, Tokyo (JP)

( * ) Notice: Subject to any disclaimer, the term of this patent is extended or adjusted under 35 U.S.C. 154(b) by 1300 days.

This patent is subject to a terminal disclaimer.

(21) Appl. No.: 12/675,174

(22) PCT Filed: Aug. 29, 2008

(86) PCT No.: PCT/JP2008/065494
§ 371 (c)(1),
(2), (4) Date: Aug. 6, 2010

(87) PCT Pub. No.: WO2009/028643
PCT Pub. Date: Mar. 5, 2009

(65) Prior Publication Data
US 2010/0291251 A1 Nov. 18, 2010

(30) Foreign Application Priority Data
Aug. 29, 2007 (JP) .................................. 2007-222476

(51) Int. Cl.
| | |
|---|---|
| A23K 20/179 | (2016.01) |
| A61K 8/99 | (2017.01) |
| A61K 31/122 | (2006.01) |
| A61Q 19/00 | (2006.01) |
| C12P 23/00 | (2006.01) |
| A61K 8/35 | (2006.01) |
| C07C 403/24 | (2006.01) |
| C09B 61/00 | (2006.01) |
| A23L 33/105 | (2016.01) |
| A23L 5/44 | (2016.01) |
| A23L 33/155 | (2016.01) |

(52) U.S. Cl.
CPC .............. *A23K 20/179* (2016.05); *A23L 5/44* (2016.08); *A23L 33/105* (2016.08); *A23L 33/155* (2016.08); *A61K 8/35* (2013.01); *A61K 8/99* (2013.01); *A61K 31/122* (2013.01); *A61Q 19/00* (2013.01); *C07C 403/24* (2013.01); *C09B 61/00* (2013.01); *C12P 23/00* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 5,607,839 A | 3/1997 | Tsubokura et al. | |
| 5,712,110 A | 1/1998 | Fleno et al. | |
| 5,789,647 A * | 8/1998 | Heidlas ................. | A23L 1/2753 585/351 |
| 5,902,890 A * | 5/1999 | Nitsche et al. ............... | 554/174 |
| 6,706,278 B1 | 3/2004 | Tsubokura et al. | |
| 7,063,956 B2 | 6/2006 | Pasamontes et al. | |
| 7,544,822 B2 * | 6/2009 | Ho ........................ | C07C 403/24 549/413 |
| 8,097,761 B2 * | 1/2012 | Ishizaki et al. ............... | 568/345 |
| 2002/0025548 A1 | 2/2002 | Sibeyn et al. | |
| 2003/0044495 A1 | 3/2003 | Kagan et al. | |
| 2003/0054070 A1* | 3/2003 | Bridges et al. .................. | 426/73 |
| 2006/0234333 A1 | 10/2006 | Matuschek et al. | |
| 2007/0196894 A1 | 8/2007 | Sim et al. | |
| 2010/0174118 A1 | 7/2010 | Ishizaki et al. | |

FOREIGN PATENT DOCUMENTS

| | | |
|---|---|---|
| CN | 1337854 A | 2/2002 |
| EP | 0543023 A1 | 5/1993 |
| EP | 0635576 A1 | 1/1995 |

(Continued)

OTHER PUBLICATIONS

Nobre et al.,Supercritical carbon dioxide extraction of astaxanthin and other carotenoids from the microalga *Haematococcus pluvialis*, 2002, Eur Food Res Technol, 223: 787-790 (Year: 2006).*
Chinese Patent Application No. 200880104826.5: Office Action, dated Mar. 1, 2012.
Examiner's Report, dated May 2, 2014, which issued during the prosecution of Canadian Patent Application No. 2,697,670, which corresponds to the present application.
A. Tsubokura et al., *Paracoccus carotinifaciens* sp. nov., a new aerobic Gram-negative astaxanthin-producing bacterium, International Journal of Systematic Bacteriology, vol. 49, pp. 277-282, 1999.
S. Machmudah et al., Extraction of Astaxanthin from Haematococcus pluvialis Using Supercritical CO2 and Ethanol as Entrainer, Ind. Eng. Chem. Res. vol. 45, pp. 3652-3657, 2006.

(Continued)

*Primary Examiner* — Amy L Clark
*Assistant Examiner* — Catheryne Chen
(74) *Attorney, Agent, or Firm* — McDermott Will & Emery LLP

(57) ABSTRACT

The present invention provides a composition comprising a high content of highly pure, low-cost, and safe carotenoid and a method for industrially producing the same. The present invention also provides functional food, a pharmaceutical composition and a cosmetic product comprising such a composition. The present invention further provides a method for producing a composition containing at least 80% of carotenoid, which is characterized in treating a microorganism culture with extraction using a lower alcohol at 80° C. at the lowest or a combination of water and a lower alcohol at 80° C. at the lowest, and then washing and filtrating the precipitate obtained from the extract solution with a combination of a lower alcohol and water.

8 Claims, No Drawings

Specification includes a Sequence Listing.

(56) References Cited

FOREIGN PATENT DOCUMENTS

| | | |
|---|---|---|
| EP | 0670306 A1 | 9/1995 |
| EP | 0719866 A1 | 7/1996 |
| EP | 0732378 A2 | 9/1996 |
| EP | 1138208 A1 | 10/2001 |
| EP | 1361281 A1 | 11/2003 |
| EP | 1430882 A2 | 6/2004 |
| EP | 2017262 A1 | 1/2009 |
| JP | 02-049091 A | 2/1990 |
| JP | 2-504101 A | 11/1990 |
| JP | 5-230387 A | 9/1993 |
| JP | 7-79796 A | 3/1995 |
| JP | 07-242621 A | 9/1995 |
| JP | 7-304978 A | 11/1995 |
| JP | 08-89280 A | 4/1996 |
| JP | 08-253695 A | 10/1996 |
| JP | 9-308481 A | 12/1997 |
| JP | 10-276721 A | 10/1998 |
| JP | 11-56346 A | 3/1999 |
| JP | 11-056346 A | 3/1999 |
| JP | 2000-515742 A | 11/2000 |
| JP | 2001-95500 A | 4/2001 |
| JP | 2001-352995 A | 12/2001 |
| JP | 2002-218994 A | 8/2002 |
| JP | 2003-144188 A | 5/2003 |
| JP | 2004-041147 A | 2/2004 |
| JP | 2004-208504 A | 7/2004 |
| JP | 2006-516293 A | 6/2006 |
| WO | 88/08025 A1 | 10/1988 |
| WO | 01/46133 A1 | 6/2001 |
| WO | 01/83437 A1 | 11/2001 |
| WO | 02/12183 A1 | 2/2002 |
| WO | WO-2005051294 * | 6/2005 |
| WO | 2006024620 A1 | 3/2006 |

OTHER PUBLICATIONS

An Office Action, dated Sep. 13, 2013, which issued during the prosecution of European Application No. 08 828 773.5, which corresponds to the present application.

L. Wang et al., Recent advances in extraction of nutraceuticals from plants, Trends in Food Science & Technology, vol. 17, pp. 300-312, 2006.

Examination Report, dated Mar. 20, 2014, which issued during the prosecution of Indian Patent Application No. 1725/CHENP/2010, which corresponds to the present application.

"Opinion of the Scientific Committee on Food on the safety in use of isopropyl alcohol and isobutyl acetate for the extraction of beta-carotene from Blakeslea trispora" dated Feb. 21, 2003, 4 pages.

* cited by examiner

METHOD FOR PRODUCTION OF CAROTENOID

CROSS REFERENCE TO PRIOR APPLICATIONS

This application is a U.S. National Phase application under 35 U.S.C. § 371 of International Application No. PCT/JP2008/065494, filed on Aug. 29, 2008 and claims benefit of priority to Japanese Patent Application No. 2007-222476, filed on Aug. 29, 2007. The International Application was published in Japanese on Mar. 5, 2009 as WO 2009/028643 under PCT Article 21(2).

TECHNICAL FIELD

The present invention relates to a method for producing carotenoid, and in particular to an industrially suitable method for producing a staxanthin usable as a component of food, pharmaceutical compositions and cosmetic products. Specifically, the present invention relates to a method of treating a microorganism culture with extraction using a lower alcohol at 80° C. at the lowest or a combination of water and a lower alcohol at 80° C. at the lowest, and is characterized in, after the extraction, washing a precipitate obtained from the extract solution with a combination of a lower alcohol and water. The present invention also relates to a method for producing a composition containing little contaminants derived from organisms and comprising at least 80% of carotenoid containing astaxanthin, the method not using an organic solvent other than a lower alcohol. The present invention further relates to a carotenoid-containing composition obtained by the method; and food, a pharmaceutical composition or a cosmetic product, comprising the carotenoid-containing composition.

BACKGROUND ART

Carotenoid is a natural pigment widely existent in the natural world, and is a polyene pigment having a color in the range of yellow to red or purple. Astaxanthin is one type of naturally-occurring carotenoid and exists in a free state or as an ester, or exists as various types of pigment proteins as a result of being bonded with proteins.

Astaxanthin is widely used as a coloring agent for fishes and chicken's eggs. Astaxanthin is also permitted to be used as a food additive and is widely used in fat and oil processed foods, protein foods, aqueous liquid foods and the like. Astaxanthin further has an anti-oxidation activity against peroxidation of lipid excited by a free radical, a singlet oxygen erasing action which can be several hundred times stronger than that of α-tocopherol or the like, and therefore is expected to be used in functional foods, cosmetic products, or medicines by utilizing the strong anti-oxidation activity thereof.

Astaxanthin is distributed widely in the natural world in, for example, fishes such as salmon, trout and red sea bream, etc.; and crustaceans such as crab, shrimp, krill, etc. Astaxanthin is also produced by bacteria belonging to *Agrobacterium, Brevibacterium* and *Paracoccus*; and microorganisms including *Haematococcus, Phaffia* yeast and the like. Carotenoid such as astaxanthin, zeaxanthin or the like is industrially produced by a chemical synthesis method, but naturally-derived carotenoid is desired from the aspect of safety.

With such a background, many methods for producing carotenoids containing astaxanthin especially derived from algae or microorganisms which are considered to be suitable to mass production have been reported.

For example, the following method for producing carotenoid from a *Haematococcus* alga has been reported (patent document 1). A cyst cell of a post-culture alga is treated with heated acetone to elute chlorophyll, which is a contaminant, then, the cyst cell is spray-dried, and carotenoid is extracted from the resultant dry cells with ethanol. However, a composition obtained by such a method still contains many contaminants derived from organisms, and is not satisfactory in terms of 1) the carotenoid content, 2) the astaxanthin content, and the like.

In order to obtain a composition containing astaxanthin at a high content, the following method, for example, has been reported (patent document 2). A crude xanthophyll obtained in conformity with the above-described method is acted on by lipase in the presence of water to decompose a neutral lipid, which is one contaminant. The lipase enzyme-treated liquid is decomposed into oil and water. From the separated oil layer, free fatty acid is separated from astaxanthin by distillation, and the astaxanthin is concentrated and purified. However, even after such complicated treating steps, a composition containing astaxanthin at a ratio exceeding 30% has not been obtained.

A method of obtaining astaxanthin contained at a ratio of 0.5 to 60% using a supercritical fluid extraction method (patent document 3) has been reported. However, an astaxanthin fraction of a content less than the targeted content is produced as a sub-product while carrying out this method. In order to discard, or increase the astaxanthin content of, such a fraction, another concentration operation is required. Therefore, this production method is not satisfactory, in terms of the simplicity and cost, as an industrial method for producing highly pure carotenoid containing a high content of astaxanthin with little contaminants derived from organisms.

As a method using *Phaffia* yeast, the following method has been reported (patent document 4). A crushed bacterial cell of the yeast is treated with extraction using an organic solvent, and the oil-like crude extraction obtained by concentrating the extract solution is purified by ion exchange chromatography, adsorption chromatography or the like to obtain astaxanthin. However, this method is performed by purifying the crude solution of low concentration astaxanthin through a plurality types of column chromatography, and so it is difficult to carry out this method in an industrial manner.

As another method, the following method has also been reported (patent document 5). A bacterial cell after the culturing of *Phaffia* yeast is treated with extraction using acetone, and the resultant extract solution is concentrated to obtain a crude extract. A hydrocarbon-based solvent is added to this crude extract to obtain crystals. This method is highly simple, but the obtained composition contains carotenoid at a content of merely about 70 to 73% (the content of astaxanthin is merely 36 to 42%). Due to such a low content, this method is not satisfactory as a method for producing highly pure carotenoid with little contaminants derived from organisms. This method is not satisfactory also for the reason that there is a concern that acetone and the hydrocarbon-based solvent may remain in carotenoid.

As methods using E-396 strain (FERM BP-4283: deposited on Apr. 27, 1993 (date of original deposition), International Patent Organism Depositary, National Institute of Advanced Industrial Science and Technology (Central 6, Higashi 1-1-1, Tsukuba-shi, Ibaraki-ken, Japan)), which is a bacterial for producing astaxanthin, adonixanthin and the like, the following methods have been reported: a method of extracting by contacting the bacterial cell to a cyclic hydrophilic organic compound, which invokes a safety concern regarding the use in food production (patent document 6); a method of using supercritical fluid extraction like patent document 3 (patent document 7); and a method of contacting E-396 strain to a water-soluble organic solvent, a non-polar solvent and water to perform liquid-liquid extraction (patent document 8).

Under these circumstances, a simpler, lower-cost method which does not require any special facilities is strongly desired to be established.

REFERENCE DOCUMENTS

Patent Document 1: Japanese Laid-Open Patent Publication No. H 11-56346
Patent Document 2: Japanese Laid-Open Patent Publication No. 2002-218994
Patent Document 3: Japanese Laid-Open Patent Publication No. 2004-41147
Patent Document 4: Japanese Laid-Open Patent Publication No. H 10-276721
Patent Document 5: Japanese Laid-Open Patent Publication No. 2004-208504
Patent Document 6: Japanese Laid-Open Patent Publication No. H 7-242621
Patent Document 7: Japanese Laid-Open Patent Publication No. H 8-89280
Patent Document 8: Japanese Laid-Open Patent Publication No. H 8-253695

DISCLOSURE OF THE INVENTION

Problems to be Solved by the Invention

The present invention has an object of providing a composition comprising highly pure carotenoid at a high content using a low-cost and safe solvent and a method for industrially producing the same, and also providing functional food, a pharmaceutical composition or a cosmetic product comprising such a composition.

Means for Solving the Problems

In order to solve the above-described problems, the present inventors conducted a research mainly on microorganism cultures and newly found the following. According to a method for industrially producing highly pure carotenoid, containing a high content of astaxanthin, with a solvent safe for food production in a simple manner without requiring special facilities or complicated operations, a microorganism culture is treated with extraction using a lower alcohol at a temperature which is equal to or lower than the boiling point of the solvent. This method requires a large amount of solvent in order to extract carotenoid from the bacterial cell, which causes a problem that a process construction cannot be done at low cost. As a result of further accumulating active studies to solve the problems including this one, the present inventors found that a highly pure carotenoid composition is obtained with a very small amount of solvent by treating a microorganism culture with extraction using a lower alcohol at 80° C. at the lowest or a combination of water and a lower alcohol at 80° C. at the lowest and then washing the precipitate, obtained by optionally concentrating the extract solution, with a combination of a lower alcohol and water. Thus, the present invention has been completed.

Namely, the present invention has the following structures.

(1) A method for extracting a carotenoid-containing composition, comprising the step of treating a microorganism culture with extraction using a lower alcohol at 80° C. at the lowest or a combination of water and a lower alcohol at 80° C. at the lowest.

(2) A method for producing a carotenoid-containing composition, comprising the following steps 1) to 4):
 1) treating a microorganism culture with extraction using a lower alcohol at 80° C. at the lowest or a combination of water and a lower alcohol at 80° C. at the lowest;
 2) obtaining a precipitate from the obtained extract solution;
 3) washing the precipitate with a lower alcohol; and
 4) further washing the precipitate with water.

(3) A method for producing a carotenoid-containing composition, comprising the following steps 1) to 3):
 1) treating a microorganism culture with extraction using a lower alcohol at 80° C. at the lowest or a combination of water and a lower alcohol at 80° C. at the lowest;
 2) obtaining a precipitate from the obtained extract solution; and
 3) washing the precipitate with a lower alcohol.

(4) The method according to any one of (1) to (3), wherein the lower alcohol is ethanol.

(5) The method according to any one of (1) to (4), wherein the carotenoid-containing composition is a composition containing at least 80% of carotenoid.

(6) The method according to any one of (1) to (5), wherein the carotenoid contains at least 40% of astaxanthin.

(7) The method according to any one of (1) to (6), wherein a DNA base sequence of the microorganism corresponding to 16S ribosomal RNA is substantially homologous to the base sequence represented by SEQ ID NO: 1.

(8) The method according to any one of (1) to (7), wherein the microorganism is E-396 strain (FERM BP-4283) or a mutant thereof.

(9) A carotenoid-containing composition obtained by the method according to any one of (1) to (8).

(10) A carotenoid-containing composition according to (9), wherein the carotenoid is in a free state.

(11) Food, a pharmaceutical composition or a cosmetic product, comprising the carotenoid-containing composition according to (9) or (10).

Effect of the Invention

The present invention can provide a composition comprising a high content of naturally-derived, highly pure, low-cost and safe carotenoid, and a method for industrially producing the same, and can also provide functional food, a pharmaceutical composition or a cosmetic product comprising such a composition.

BEST MODE FOR CARRYING OUT THE INVENTION

Hereinafter, embodiments of the present invention will be specifically described. The scope of the present invention is not limited to the following description, and may be carried out in appropriate modifications other than the following illustrative embodiments without departing from the spirit of the present invention.

All the publications cited herein, for example, the related art documents, laid-open patent publications, patent publications, and other patent-related documents, are incorporated herein in their entirety for reference. The specification of Japanese Patent Application No. 2007-222476, upon which the present application claims the benefit of priority, is incorporated herein.

The microorganisms usable for the present invention include, without limitation, any microorganism capable of producing carotenoid. For example, *Paracoccus* bacteria, *Haematococcus* algae, *Phaffia* yeasts and the like are usable. Examples of the *Paracoccus* bacteria include *Paracoccus carotinifaciens, Paracoccus marcusii, Paracoccus haeundaensis, Paracoccus zeaxanthinifaciens, Paracoccus denitrificans, Paracoccus aminovorans, Paracoccus aminophilus, Paracoccus kourii, Paracoccus halodenitrificans*, and *Paracoccus alcaliphilus*. Examples of the *Haematococcus* algae include *Haematococcus pluvialis, Haematococcus lacustris, Haematococcus capensis, Haematococcus droebakensis*, and *Haematococcus zimbabwiensis*. Examples of the *Phaffia* yeasts include *Phaffia rhodozyma*. The microorganisms usable in the present invention are not limited to the above.

Especially from the viewpoint of the proliferation speed and carotenoid productivity, a bacterium, of which the DNA base sequence corresponding to 16S ribosomal RNA is substantially homologous to the base sequence represented by SEQ ID NO: 1 in the sequence listing, is preferable.

The expression "substantially homologous" means that these sequences have homology of 94% or higher, preferably 96% or higher, and more preferably 98% or higher, in consideration of the error frequency in determining the base sequence of DNA, and the like. Among such bacteria, E-396 strain (FERM BP-4283) is especially preferable. It is also very preferable to use a strain highly productive of carotenoid, the strain being obtained by mutating these microorganisms for the purpose of improving the productivity of carotenoid.

The E-396 strain is deposited as international deposition to the International Patent Organism Depositary, National Institute of Advanced Industrial Science and Technology as follows:

International Deposition Authority: International Patent Organism Depositary, National Institute of Advanced Industrial Science and Technology (former National Institute of Bioscience and Human-Technology, Agency of Industrial Science and Technology, Ministry of International Trade and Industry)

Chuoh 6, Higashi 1-1-1, Tsukuba-shi, Ibaraki-ken, 305-8566

Identification No.: E-396

Deposition No.: FERM BP-4283

Date of original deposition: Apr. 27, 1993

There is no specific limitation on the method for producing a mutant as long as the method induces mutation. Usable methods include, for example, a chemical method using a mutating agent such as N-methyl-N'-nitro-N-nitrosoguanidine (NTG), ethylmethanesulfonate (EMS) or the like; a physical method using ultraviolet radiation, x-ray radiation or the like; or a biological method using gene recombination, transposon or the like. The mutation may be performed in one stage, or two or more stages. In the latter case, for example, a mutant of an astaxanthin-producing microorganism is obtained by the above mutation process, and then the obtained mutant is further subjected to another mutation process.

A microorganism culture, etc. usable for the present invention may be any culture, without specific limitation, which is obtained by a method capable of culturing the above-described microorganism efficiently, for example, by a method of using liquid culture, solid culture or a combination thereof using any of the following mediums.

A nutrition medium usable for culturing a microorganism used for the present invention may be any nutrition medium containing a carbon source, a nitrogen source and an inorganic salt necessary for growing a production bacterium. It may be more preferable to add a vitamin. It may be preferable to further add amino acid, nucleic acid base or the like. Other substances which may be optionally added include yeast extract, peptone, meat extract, malt extract, corn steep liquor, dry yeast, soybean cake and the like.

Usable carbon sources include sugars such as glucose, sucrose, lactose, fructose, trehalose, mannose, mannitol, maltose and the like; organic acids such as acetic acid, fumaric acid, citric acid, propionic acid, malic acid, malonic acid, pyruvic acid and the like; alcohols such as ethanol, propanol, butanol, pentanol, hexanol, isobutanol, glycerol and the like; fats and oils such as soybean oil, rice bran oil, olive oil, corn oil, sesame oil, linseed oil and the like; etc. These carbon sources may be used independently or in a combination of two or more. The ratio thereof depends on the type of the carbon source and may be appropriately adjusted, but usually is 1 to 100 g, preferably 2 to 50 g, per 1 L of the medium.

Usable nitrogen sources include, for example, potassium nitrate, ammonium nitrate, ammonium sulfate, ammonium chloride, ammonium phosphate, ammonia, urea and the like. These nitrogen sources may be used independently or in a combination of two or more. The ratio thereof depends on the type of the nitrogen source and may be appropriately adjusted, but usually is 0.1 to 30 g, preferably 1 to 10 g, per 1 L of the medium.

Usable inorganic salts include potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium carbonate, and the like. These inorganic salts may be used independently or in a combination of two or more. The ratio thereof depends on the type of the inorganic salt and may be appropriately adjusted, but usually is 0.001 to 10 g, per 1 L of the medium.

When a vitamin is added, the amount thereof depends on the type of the vitamin and may be appropriately adjusted, but usually is 0.1 to 1000 mg, preferably 1 to 100 mg, per 1 L of the medium.

The amount of each of amino acid, nucleic acid base, yeast extract, peptone, meat extract, malt extract, corn steep liquor, dry yeast, soybean cake and the like depends on the type of the substance and may be appropriately adjusted, but usually is 0.2 g to 200 g, preferably 3 to 100 g, per 1 L of the medium.

The pH of the medium is adjusted to 2 to 12, preferably 6 to 9. The culturing is performed at a temperature of 15 to 80° C., preferably 20 to 35° C., for 1 to 20 days, preferably 2 to 8 days, under an aerobic condition. The aerobic condition is, for example, shaking culture, aeration and stirring culture, or the like.

According to a preferable method for extracting astaxanthin produced by a cultured microorganism used for the present invention, the culture solution, or a bacterial cell concentrated solution, a wet bacterial cell or a dry bacterial cell obtained from the culture solution is treated with extraction as follows after the culturing. The bacterial cell concentrated solution can be obtained by treating the culture solution with, for example, concentration by membrane filtration. The wet bacterial cell can be obtained by treating the culture solution with centrifugation, pressurization, filtration at reduced pressure, or any other generally known filtration method. The dry bacterial cell can be obtained by drying the wet bacterial cell using atomization drying, fluidized drying, rotating drum drying, lyophilization or any other generally known drying method. It is also recommended that before performing the following extraction, the culture solution, the bacterial cell concentrated solution, the wet bacterial cell or the dry bacterial cell is treated with one, or at least two, of a chemical treatment using an alkaline reagent, a surfactant or the like; a biochemical treatment using a bacteriolytic enzyme, a lipid decomposing enzyme, a proteolytic enzyme or the like; and a physical treatment using ultrasonic waves, pulverization or the like. The dry bacterial cell is usually considered to contain astaxanthin at a ratio of about 20 mg/g.

Examples of the solvent usable for extraction and washing in the present invention include lower alcohols, for example, lower alcohols having a carbon number of 1 to 6, preferably 1 to 3. Specifically, ethanol, methanol, isopropanol and the like are preferable; and ethanol is especially preferable. A mixture of two or more of these lower alcohols may be used. The temperature of a lower alcohol at the time of extraction is 80° C. at the lowest, preferably 80° C. or higher, more preferably 85° C. or higher, still more preferably 90° C. or higher, and especially preferably 93° C. higher.

Herein, the expression "at the lowest" refers to the lowest temperature at which the lower alcohol should be kept at the time of extraction.

The temperature at the time of extraction is related with an increase of the solubility of astaxanthin-containing carotenoid in ethanol, and so is an important factor for increasing the extraction efficiency. The upper limit on the temperature of the lower alcohol at the time of extraction is preferably 150° C. or lower, more preferably 130° C. or lower, still more preferably 120° C. or lower, especially preferably 110° C. or lower, and most preferably 100° C. or lower. The upper limit on the temperature is important to suppress the thermal decomposition of carotenoid containing astaxanthin. Accordingly, the range of the temperature of the lower alcohol used in the present invention at the time of extraction is, for example, 80° C. to 150° C., preferably 85° C. to 120° C., more preferably 90° C. to 110° C., and especially preferably around 95° C.

For the above, a temperature of the boiling point or higher, or around the boiling point, of the solvent is necessary. Therefore, the treatment needs to be performed in a sealed pressure vessel. The gauge pressure at this point is 0.8 MPa at the maximum, preferably 0.4 MPa or lower, and more preferably 0.2 MPa or lower.

The amount of the lower alcohol, which is defined by the temperature at the time of extraction, may be any amount with which the amount of astaxanthin contained in the bacterial cell can be dissolved. In the case of extraction from a dry bacterial cell with a lower alcohol, the amount is 300 to 3,000 g, preferably 500 to 2,000 g, and more preferably 800 to 1,600 g, per 1 g of astaxanthin contained in the bacterial cell.

For example, when extraction is performed with ethanol at 95° C. from 1 g of dry bacterial cell containing about 20 mg of astaxanthin, the amount of ethanol may be about 5 g to 100 g, preferably 8 g to 60 g, and more preferably about 10 g to 35 g.

During the extraction, the pigment in the bacterial cell is made easier to be extracted by adding water. Therefore, water may be added to the lower alcohol for extraction. In the case where water is added to the lower alcohol, the ratio of the water is about 1/400 to 1/5, preferably about 1/300 to 1/10, and more preferably 1/200 to 1/15, of the volume of the lower alcohol.

By adding water before adding the lower alcohol, the surface of the dry bacteria cell is wetted and thus the lower alcohol added later is made easier to be incorporated into the bacterial cell. This raises the extraction efficiency of carotenoid by about 5 to 10%. Therefore, when water is added, it is desirable to add water before the lower alcohol is added to the bacterial cell. In addition, a mixture of the lower alcohol and water may be used for the extraction. There is no specific limitation on the mixing ratio, but is 1:10 to 1:100, preferably 1:20 to 1:40.

When a dry material is used, it is desirable to add water. However, in the case where the pigment is extracted from a sample having a high water content, such as a viable cell, a live sample or the like, the concentration of the lower alcohol is decreased by adding water, and the extraction efficiency is lowered. For this reason, it is necessary to check the water content of the material from which extraction is to be performed and determine whether or not to add water.

When it is desired to suppress oxidation of carotenoid during the extraction operation to a minimum possible level, the extraction may be performed under an atmosphere of an inert gas such as nitrogen gas, or an antioxidant used for medicines or foods may be appropriately selected and added to the extraction solvent. These treatments may be combined.

It is desirable that the antioxidant is removed from the carotenoid composition in the end, but removal may not be necessary depending on the type of the antioxidant used (for example, when vitamin C is used).

In order to suppress the decomposition of carotenoid caused by light to a minimum possible level, the extraction may be performed under conditions with no light radiation.

There is no specific limitation on the extraction time. For suppressing the reduction of the yield caused by thermal decomposition, it is preferable to complete the treatment within a short time. The extraction time is preferably within 120 minutes, more preferably within 60 minutes, and most preferably within 30 minutes.

Any method is usable to separate the extract solution from the microorganism after the extraction operation. Membrane filtration, centrifugation, decantation and the like are usable. For an industrial use, centrifugation is preferable. For an industrial use, there is no specific limitation on the temperature for separation. The carotenoid pigment which is extracted at high temperature of 80° C. or higher and dissolved in a lower alcohol is in a supercooled state, and so is not easily deposited within a short time even when being cooled to −20° C. to 70° C. Therefore, the extract solution can be separated stably even at low temperature.

In general, methods for obtaining a precipitate from an extract solution obtained by treating a microorganism culture with extraction using a lower alcohol include heating and/or concentration at reduced pressure and precipitation. Alternatively, the carotenoid pigment may be separated, without being concentrated, by deposition of the carotenoid pigment at low temperature or deposition using an acid or alkaline agent or any of various salts. In this operation, the carotenoid pigment is recovered from the supercooled state when being left at room temperature for 1 hour or longer and thus can be deposited. The recovery from the supercooled state can be expedited by stirring or vibrating the carotenoid pigment. However, the supercooled state is varied in accordance with the extraction temperature, and so a condition for recovery from the supercooled state, which is suitable to the extraction temperature, needs to be selected.

By performing the operations described above, free trans carotenoid can be obtained. When being recovered from the supercooled state by the above-described operation, the free trans astaxanthin is not highly soluble in ethanol at room temperature. Even where ethanol is added, the trans astaxanthin is not dissolved and is suspended.

As to concentrating the carotenoid pigment, the degree of concentration may be appropriately determined in consideration of the amount and the purity of the precipitate to be obtained. For example, the extract solution may be concentrated 10- to 1000-fold, preferably 30- to 500-fold, more preferably 50- to 400-fold, and especially preferably 100- to 200-fold, with respect to the weight thereof. Most preferably, the solvent in the extract solution is completely removed by distillation and the carotenoid pigment is dried.

The solution removed by concentrating the extract solution may be reused for extraction from a cultured microorganism with no further treatment.

For an industrial use, precipitation is desirable. This can be realized by, for example, cooling the solution, adding a new solvent which decreases the solubility of the solute, or changing the pH.

A dried precipitate, a concentrated precipitate, or a deposited precipitate is optionally suspended and stirred using a small amount of lower alcohol for washing. Regarding an amount of the lower alcohol used for suspending the precipitate recovered from the supercooled state, it is desirable to select an industrially durable amount in consideration of the purity of the precipitate. For example, the amount may be as small as about twice, but may be greater than that, preferably 4 times or greater, more preferably 8 times or greater, still more preferably 16 times or greater, and even 32 times or greater when necessary, per 1 g of the dried precipitate. When a concentrated precipitate is used, a weight in the dry state should be used, which is calculated using a conversion coefficient that can be set by checking, before drying, the correlation between the volume or weight of the undried precipitate and that of the dried precipitate.

In order to raise the purity of the precipitate, the precipitate may be put into smaller pieces by use of physical treatment such as ultrasonic waves or pulverization, before being suspended in a lower alcohol. Detailed conditions for this operation may be appropriately determined in accordance with the purity of the obtained precipitate.

There is no specific limitation on the washing method. Practically preferable methods include, for example, a method of performing filtration after the precipitate is suspended and stirred, a method of passing the solution from above the precipitate, and the like. The temperature at the time of washing is preferably in the range of 1° C. to 30° C. in general, but may be lower than 1° C. or higher than 30° C. depending on the situation. The upper limit on the temperature may be around the boiling point of the lower alcohol, at which the solubility in the lower alcohol is increased, and is preferably the boiling point or lower.

When the precipitate is washed with a lower alcohol, free trans astaxanthin is not highly soluble, but free cis astaxanthin which becomes cis because of the high temperature is highly soluble in ethanol. Therefore, as a result of filtration and washing, only the free trans astaxanthin is left as a solid and can be distinguished from the cis astaxanthin. As used herein, term "free astaxanthin" refers to astaxanthin which is not ester-linked with fatty acid and is in a state where two hydroxyl groups are bonded to a basic structure.

It is possible to recover the used lower alcohol from the waste fluid which is generated during the washing performed to obtain highly pure carotenoid from the precipitate, using a method of distillation or of removal by distillation at reduced pressure, so that the recovered lower alcohol can be reused for another washing step as a solvent.

In order to reduce the amount of the solvent remaining in the carotenoid-containing composition according to the present invention after the washing and drying, a step of washing with water to be substituted for the solvent may be added at the end of the washing.

This operation of washing with water can remove the water-soluble fraction, and so the purity of carotenoid can be improved by about 2 to 10%.

In order to maximize the contents of carotenoid and the main components such as astaxanthin and the like in the carotenoid-containing composition obtained by the above-described method, the conditions of the above-described purification steps may be appropriately adjusted. The content of carotenoid in the carotenoid-containing composition according to the present invention is defined by the amount of astaxanthin in the carotenoid in the bacterial cell. The content of carotenoid in the carotenoid-containing composition obtained according to the present invention is at least 80%, for example, 80% or greater, preferably 85% or greater, more preferably 88% or greater, and most preferably 90% or greater. The content of astaxanthin in the carotenoid is at least 40%, for example, 40% or greater, preferably 43% or greater, more preferably 44% or greater, and most preferably 48% or greater.

As used herein, the expression "at least" refers to the lowest content at which carotenoid should be contained in the composition. The same is applied to astaxanthin.

Where E-396 strain or a mutant thereof is used as the bacterial cell, a carotenoid-containing composition containing astaxanthin at 40% or greater with respect to the entire carotenoid in the composition can be obtained.

As described above, the method according to the present invention is characterized in treating a microorganism culture with extraction using a lower alcohol at 80° C. at the lowest or a combination of water and a lower alcohol at 80° C. at the lowest and then washing, with a combination of a lower alcohol and water, the precipitate which is obtained by, for example, concentrating, drying and solidifying the extract solution. Carotenoid can be obtained at a high level of purity merely by these very simple operations. By performing extraction at high temperature, the amount of the solvent to be used can be significantly decreased.

The method according to the present invention is significantly industrially advantageous over the conventional art on the points of 1) not requiring a complicated operation; 2) not requiring an inefficient purification operation such as increasing the purity of a low concentration solution; and 3) not using a large amount of solvent for extraction. The present invention has a meritorious effect of realizing a superior industrial production method on the points of 4) providing a highly pure carotenoid composition containing astaxanthin at a high content, at low cost and 5) allowing the solvent used in each step to be easily recovered and reused.

Foods, pharmaceutical compositions, and cosmetic products comprising a carotenoid-containing composition according to the present invention are encompassed in the present invention.

Medicines comprising highly pure carotenoid containing astaxanthin at a high content produced by a production method according to the present invention are available in formulations including powder, granule, pill, soft capsule, hard capsule, tablet, chewable tablet, disintegrating tablet, syrup, solution, suspension, suppository, ointment, cream, gel, sticky medicine, inhalant, injection and the like. These formulations are prepared in accordance with an established method. Carotenoid is not highly soluble in water, and so is used as being dissolved in a non-hydrophilic organic solvent such as a vegetable oil, an animal oil or the like, as being dispersed or emulsified in an aqueous solution together with an emulsifier, a dispersant, a surfactant or the like using a homogenizer (high pressure homogenizer), or being dissolved by heat. In order to improve the capability of carotenoid of being absorbed, carotenoid may be used after being pulverized to an average particle diameter as small as about 1 micrometer.

Additives usable for producing the formulations include, for example, animal and vegetable oils including soybean oil, saffron oil, olive oil, germ oil, sunflower oil, grape seed oil, beef tallow, sardine oil and the like; polyhydric alcohols including polyethylene glycol, propylene glycol, glycerin, sorbitol and the like; surfactants including sorbitan fatty acid ester, sucrose fatty acid ester, glycerin fatty acid ester, polyglycerin fatty acid ester and the like; excipients including purified water, lactose, starch, crystalline cellulose, D-mannitol, lecithin, gum arabic, sorbitol solution, sugar solution and the like; sweeteners, coloring agents, pH adjusters, flavor substances, etc. A liquid formulation may be dissolved or suspended in water or any other appropriate medium when being administered. A tablet or a granule may be coated by a well known method, or wrapped in a sol- or gel-like substance or the like.

Administration by injection is preferably performed intravenously, intraperitoneally, intramuscularly, subcutaneously, percutaneously, intra-articularly, in synovial bursa, in bulla, in periosteum, sublingually, orally or the like, and is especially preferably performed intravenously or intraperitoneally. The intravenous administration may be drip administration or bolus administration.

When carotenoid is used as a medicine, the daily dose for an adult is 1 mg to 3 g, preferably 3 mg to 1 g, and more preferably 10 mg to 670 mg. When converted to an amount per 1 kg of the body weight, such doses are respectively, 17 µg to 50 mg, 54 µg to 17 mg, and 160 µg to 12 mg. Such a dose is administered once a day or as being divided to several times a day. The pharmaceutically effective amount, administration method, administration means and administration period can be appropriately set by a person of ordinary skill in the art in accordance with the clinical state, gender, age, body weight or the like of each administration target.

Foods comprising highly pure carotenoid containing astaxanthin at a high content according to the present invention are available as, for example, supplements (powder, granule, soft capsule, hard capsule, tablet, chewable tablet, disintegrating tablet, syrup, solution, etc.), drinks (tea, carbonated drink, lactic drink, sports drink, etc.), confectionaries (gummi, jelly, chewing gum, chocolate, cookie, candy, etc.), oils, fats and oils foods (mayonnaise, dressing, butter, cream, margarine, etc.), seasonings (ketchup, sauce, etc.), liquid foods, dairy products (milk, yogurt, cheese, etc.), breads, noodles (udon, soba, ramen, pasta, fried noodle, kishimen, somen, hiyamugi, bihon, etc.), and the like. The foods are not limited to the above.

Functional foods comprising highly pure carotenoid containing astaxanthin at a high content according to the present invention may optionally contain any of various nutrients, various vitamins (vitamin A, vitamin B1, vitamin B2, vitamin B6, vitamin B12, vitamin C, vitamin E, etc.), various minerals, dietary fiber, polyunsaturated fatty acid, other nutrients (coenzyme Q10, carnitine, sesamine, α-lipoic acid, inositol, D-chiroinositol, pinitol, phosphatidylserine, phosphatidyl DHA, phosphatidyl inositol, taurine, glucosamine, chondroitin sulfate, S-adenosylmethionine, etc.), stabilizers such as, for example, dispersants and emulsifiers, sweeteners, taste enriching components (citric acid, malic acid, etc.), flavor substances, royal jelly, propolis, agaricus, and the like. Herbs such as peppermint, bergamot, chamomile, lavender, thyme, and the like can be also contained. Elements such as theanine, dehydroepiandrosterone, melatonin and the like can be also contained.

Cosmetic products comprising highly pure carotenoid containing astaxanthin at a high content according to the present invention include cream, milky lotion, lotion, microemulsion essence, bathwater additive and the like, and may contain aromatic essence or the like.

When carotenoid is used as food or a supplement, there is no specific limitation on the dose or administration manner. The dose may be 17 µg to 50 mg, preferably 54 µg to 17 mg, and more preferably 160 µg to 12 mg, when converted to the dose per 1 kg of the body weight.

When carotenoid is used as a cosmetic product, the dose is 10 µg to 5 g, preferably 10 µg to 2 g, and more preferably 10 µg to 1 g, per 100 g of the cosmetic product.

EXAMPLES

The present invention will be described based on examples, reference examples, formulation examples and test examples. The scope of the present invention is not limited to the following examples.

In the examples and comparative examples, astaxanthin and carotenoid were quantified by high performance liquid chromatography (HPLC). Two columns of Wakosil-II SIL-100 (φ4.6×250 mm) (produced by Wako Pure Chemical Industries, Ltd.) were connected to each other to be used as a column. Elution was performed by flowing an n-hexane-tetrahydrofuran-methanol mixed solution (40:20:1), which was a mobile phase, at a flow rate of 1.0 ml/min. at a constant temperature around room temperature. The measurement was performed as follows. The sample was dissolved in tetrahydrofuran, and the resultant substance was diluted 100-fold with the mobile phase. 20 µL of the resultant solution was injected. The column elution solution was detected at a wavelength of 470 nm. As the reference product for quantification, astaxanthin produced by Sigma (Cat. No. A9335) was used. The astaxanthin concentration of the reference solution was set using the following expression after measuring the absorbance of the reference solution of 477 nm (A) and the area percentage % (B) of the astaxanthin peak at the time of HPLC analysis under the above-described conditions.

$$\text{Astaxanthin concentration(mg/L)} = A \div 2150 \times B \times 100$$

[Example 1] Production of Highly Pure Carotenoid Containing Astaxanthin at a High Content—1

Step 1: Step of Extracting with Ethanol

To 13 g of dry bacterial cells obtained by culturing E-396 strain (FERM BP-4283) and containing 20 mg of astaxanthin per 1 g, 200 g of ethanol was added, and while stirring the resultant substance at 95° C. for 30 minutes in a nitrogen-substituted atmosphere in a high pressure vessel, carotenoid containing astaxanthin was extracted. The resultant substance was cooled down to 30° C., and then the bacterial cells were removed by filtration. The bacterial cell cake was washed with ethanol to obtain 300 g of extract solution containing 0.14% (wt./wt.) of astaxanthin and having a carotenoid weight concentration of 0.36% (wt./wt.).

Step 2: Step of Concentrating the Extract Solution, and Depositing 300 g of the extract solution obtained in step 1 of this example was concentrated at reduced pressure using an evaporator to obtain a concentrated dry solid (about 2 g) containing a precipitate and also a removed solution (about 300 g of ethanol).

Step 3: Step of Filtrating the Precipitate, Washing and Drying

To about 2 g of the concentrated dry solid obtained in step 2 of this example, 20 g of ethanol was added, and the resultant substance was suspended and washed, and filtrated. The filtrate was washed with 10 g of water, and then dried at room temperature at reduced pressure to obtain 0.2 g of dried precipitate. The contents of astaxanthin and carotenoid in this dried substance were 43% and 86%, respectively.

[Example 2] Production of Highly Pure Carotenoid Containing Astaxanthin at a High Content—2

Step 1: Step of Extracting with Ethanol

To 13 g of dry bacterial cells obtained by culturing E-396 strain (FERM BP-4283) and containing 20 mg of astaxanthin per 1 g, 200 g of ethanol and 10 g of water were added, and while stirring the resultant substance at 95° C. for 30 minutes in a nitrogen-substituted atmosphere in a high pressure vessel, carotenoid containing astaxanthin was extracted. The resultant substance was cooled down to 30° C., and then the bacterial cells were removed by filtration. The bacterial cell cake was washed with ethanol to obtain 300 g of extract solution containing 0.16% (wt./wt.) of astaxanthin and having a carotenoid weight concentration of 0.38% (wt./wt.).

Step 2: Step of Concentrating the Extract Solution, and Depositing 300 g of the extract solution obtained in step 1 of this example was concentrated at reduced pressure using an evaporator to obtain a concentrated dry solid (about 2 g) containing a precipitate and also a removed solution (about 300 g of ethanol).

Step 3: Step of Filtrating the Precipitate, Washing and Drying

To about 2 g of the concentrated dry solid obtained in step 2 of Example 1, 20 g of ethanol was added, and the resultant substance was suspended and washed, and filtrated. The filtrate was washed with 10 g of water, and then dried at room temperature at reduced pressure to obtain 0.2 g of dried precipitate. The contents of astaxanthin and carotenoid in this dried substance were 48% and 88%, respectively.

[Example 3] Production of Highly Pure Carotenoid Containing Astaxanthin at a High Content—3

Step 1: Step of Extracting with Ethanol

To 13 g of dry bacterial cells obtained by culturing E-396 strain (FERM BP-4283) and containing 20 mg of astaxanthin per 1 g was treated with extraction of carotenoid and filtration in conformity with step 1 of Example 2 to obtain 300 g of extract solution.

Step 2: Step of Concentrating the Extract Solution, and Depositing

The extraction of carotenoid and filtration were performed in conformity with step 2 of Example 1 to obtain 300 g of extract solution. The extract solution was concentrated at reduced pressure in conformity with step 2 of Example 1 to obtain about 2 g of concentrated dry solid.

Step 3: Step of Filtrating the Precipitate, Washing and Drying

To about 2 g of the concentrated dry solid obtained in step 2 of Example 3, 20 g of ethanol was added, and the resultant substance was suspended and washed, and filtrated. The filtrate was dried at room temperature at reduced pressure to obtain 0.25 g of dried precipitate. The contents of astaxanthin and carotenoid in this dried substance were 44% and 80%, respectively.

It was confirmed that by eliminating the step of washing with water, the purity is lowered but the recovered amount is increased.

[Example 4] Production of Highly Pure Carotenoid Containing Astaxanthin at a High Content—4

A small amount of ethanol was added to a sample of salmon flesh, and the salmon was minced by a food processor. Then, the minced salmon was treated with extraction of carotenoid and filtration in conformity with step 1 of Example 1 to obtain an extract solution. The extract solution was concentrated at reduced pressure in conformity with step 2 of Example 1 to obtain a concentrated dry solid. The concentrated dry solid was filtrated in conformity with step 3 of Example 1 to obtain a precipitate, and the precipitate was washed and dried to obtain a dried substance. The dried substance was examined to find that the content of carotenoid was 60% of the content of carotenoid in salmon.

It is known that for extracting carotenoid from a fish flesh sample, a plurality of cycles of extraction operation is performed in repetition. The amount of carotenoid obtained by carrying out one cycle of the carotenoid extraction method according to the present invention was equivalent to the amount of carotenoid obtained by carrying out the first cycle of carotenoid extraction performed in conformity with an established method.

[Example 5] Production of Highly Pure Carotenoid Containing Astaxanthin at a High Content Using a Recovered Solvent—1

To 13 g of dry bacterial cells of E-396 strain substantially the same as those used in Example 1, 200 g of the removed solution (ethanol) obtained in step 1 of Example 1 was added, and the resultant substance was treated with extraction of carotenoid and filtration of the bacterial cells in conformity with step 1 of Example 1 to obtain 300 g of extract solution. The extract solution was concentrated at reduced pressure in conformity with step 2 of Example 1 to obtain about 2 g of concentrated dry solid. The concentrated dry solid was filtrated in conformity with step 3 of Example 1 to obtain a precipitate, and the precipitate was washed and dried to obtain 0.2 g of dried substance. The contents of astaxanthin and carotenoid in this dried substance were 43% and 86%, respectively.

From the above, it was confirmed that reuse of the recovered ethanol presents no problem.

[Example 6] Production of Highly Pure Carotenoid Containing Astaxanthin at a High Content Using a Recovered Solvent—2

To 13 g of dry bacterial cells of E-396 strain substantially the same as those used in Example 1, 200 g of the removed solution (ethanol) obtained in step 1 of Example 1 was added, and the resultant substance was treated with extraction of carotenoid and filtration of the bacterial cells in conformity with step 1 of Example 1 to obtain 300 g of extract solution. The extract solution was concentrated at reduced pressure in conformity with step 2 of Example 1 to obtain about 2 g of concentrated dry solid. To the concentrated dry solid, 20 g of the recovered ethanol obtained in step 2 of Example 1 was added, and the resultant substance was suspended and filtrated. The filtrate was washed with 10 g of water, and then dried at room temperature at reduced pressure to obtain 0.2 g of dried precipitate. The contents of astaxanthin and carotenoid in this dried substance were 43% and 86%, respectively.

From the above, it was confirmed that use of the ethanol recovered as a result of removal by distillation at reduced pressure presents no problem to the washing step.

[Food Example 1] Margarine

The astaxanthin composition obtained in Example 1 was added as an antioxidant and coloring agent to vegetable oil such that the astaxanthin composition would be contained at 5% by weight of margarine. The resultant substance was stirred together with an emulsifier and the like so as to be uniform, and margarine was produced by a usual method. As compared with usual margarine, the obtained margarine exhibited a pale red color because of the presence of astaxanthin.

[Food Example 2] Olive Oil

The astaxanthin composition obtained in Example 1 was added such that the astaxanthin composition would be contained at 0.25% by weight of olive oil. The resultant substance was stirred at 50° C., dissolved and then cooled down to room temperature. As compared with usual olive oil, the obtained olive oil exhibited a deep red color because of the presence of astaxanthin. By changing the amount of the astaxanthin composition, the depth of the color was changed. Even after being left for a long time, astaxanthin, once dissolved, was not deposited.

[Formulation Example 1] Astaxanthin-Containing Tablet

To 120 parts by weight of the carotenoid-containing composition obtained in Example 1, 330 parts by weight of crystalline cellulose, 15 parts by weight of carmellose-calcium, 10 parts by weight of hydroxypropyl cellulose and 60 parts by weight of purified water were mixed in a usual method, and the resultant substance was dried. Then, 10 parts by weight of magnesium stearate was added thereto, and the resultant substance was tableted to obtain 100 mg of tablets containing a carotenoid-containing composition at a ratio of 20 mg/piece.

[Formulation Example 2] Astaxanthin-Containing Soft Capsule

One part by weight of the carotenoid-containing composition obtained in Example 1 was suspended in soybean oil of a part by weight 5 times larger, and the substances were sufficiently mixed so as to be uniform. Then, the resultant substance was filled into capsules by a capsule filler to obtain reddish brown capsules each containing 300 mg.

[Cosmetic Example 1] Astaxanthin-Containing Cream (Cosmetic Product)

The astaxanthin-containing composition obtained in Example 1 was added to white petrolatum so as to be contained at a ratio of 10% by weight, and the resultant substance was dispersed together with an aromatic substance and the like so as to be uniform. Then, cream was produced by a usual method.

INDUSTRIAL APPLICABILITY

The present invention can provide a composition comprising a high content of naturally-derived, highly pure, low-cost and safe carotenoid, and a method for industrially producing the same. Hence, the present invention can also provide functional food, a pharmaceutical composition and a cosmetic product comprising such a composition.

Sequence Listing Free Text

SEQ ID NO: 1: Explanation on unknown organism: E-396

The invention claimed is:

1. A method for extracting a carotenoid-containing composition, comprising the step of extracting a microorganism culture with a solvent including a lower alcohol having a carbon number of 1 to 3 at a temperature from 80° C. to 150° C., or a combination of water and a lower alcohol having a carbon number of 1 to 3, at a temperature from 80° C. to 150° C. to provide an extract solution, wherein the extracting step is performed in a sealed pressure vessel above atmospheric pressure and at a maximum gauge pressure of 0.4 MPa.

2. A method for producing a carotenoid-containing composition, comprising the following steps:
   extracting a microorganism culture with a solvent including a lower alcohol having a carbon number of 1 to 3 at a temperature from 80° C. to 150° C., or a combination of water and a lower alcohol having a carbon number of 1 to 3 at a temperature from 80° C. to 150° C. to form an extract solution;
   obtaining a precipitate from the obtained extract solution;
   washing the precipitate with a lower alcohol having a carbon number of 1 to 3; and
   further washing the precipitate with water, wherein the extracting step is performed in a sealed pressure vessel above atmospheric pressure and at a maximum gauge pressure of 0.4 MPa.

3. A method for producing a carotenoid-containing composition, comprising the following steps:
   extracting a microorganism culture with a solvent including a lower alcohol having a carbon number of 1 to 3 at a temperature from 80° C. to 150° C., or a combination of water and a lower alcohol having a carbon number of 1 to 3 at a temperature from 80° C. to 150° C. to form an extract solution;
   obtaining a precipitate from the obtained extract solution; and
   washing the precipitate with a lower alcohol having a carbon number of 1 to 3, wherein the extracting step is performed in a sealed pressure vessel above atmospheric pressure and at a maximum gauge pressure of 0.4 MPa.

4. The method according to claim 1, wherein the lower alcohol is ethanol.

5. The method according to claim 1, wherein the carotenoid-containing composition is a composition containing at least 80% of the carotenoid.

6. The method according to claim 1, wherein the carotenoid contains at least 40% astaxanthin.

7. The method according to claim 1, wherein the microorganism has a DNA base sequence corresponding to 16S ribosomal RNA, which is substantially homologous to the base sequence represented by SEQ ID NO: 1.

8. The method according to claim 1, wherein the microorganism is E-396 strain (FERM BP-4283) or a mutant thereof.

* * * * *

SEQUENCE LISTING

```
<160> NUMBER OF SEQ ID NOS: 1

<210> SEQ ID NO 1
<211> LENGTH: 1452
<212> TYPE: DNA
<213> ORGANISM: Unknown
<220> FEATURE:
<223> OTHER INFORMATION: Description of Unknown Organism:E-396
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga        60
gaccttcggg tctagcggcg gacgggtgag taacgcgtgg gaacgtgccc ttctctacgg       120
aatagccccg ggaaactggg agtaataccg tatacgccct ttgggggaaa gatttatcgg       180
agaaggatcg gcccgcgttg gattaggtag ttggtggggt aatggcccac caagccgacg       240
```

-continued

```
atccatagct ggtttgagag gatgatcagc cacactggga ctgagacacg gcccagactc    300
ctacgggagg cagcagtggg gaatcttaga caatgggggc aaccctgatc tagccatgcc    360
gcgtgagtga tgaaggcctt agggttgtaa agctctttca gctgggaaga taatgacggt    420
accagcagaa gaagccccgg ctaactccgt gccagcagcc gcggtaatac ggaggggggct   480 agcgttgttc ggaattactg ggcgtaaagc gcacgtaggc ggactggaaa gtcagaggtg    540
aaatcccagg gctcaacctt ggaactgcct ttgaaactat cagtctggag ttcgagagag    600
gtgagtggaa ttccgagtgt agaggtgaaa ttcgtagata ttcggaggaa caccagtggc    660
gaaggcggct cactggctcg atactgacgc tgaggtgcga aagcgtgggg agcaaacagg    720
attagatacc ctggtagtcc acgccgtaaa cgatgaatgc cagacgtcgg caagcatgct    780
tgtcggtgtc acacctaacg gattaagcat tccgcctggg gagtacggtc gcaagattaa    840
aactcaaagg aattgacggg ggcccgcaca agcggtggag catgtggttt aattcgaagc    900
aacgcgcaga accttaccaa cccttgacat ggcaggaccg ctggagagat tcagctttct    960
cgtaagagac ctgcacacag gtgctgcatg gctgtcgtca gctcgtgtcg tgagatgttc   1020
ggttaagtcc ggcaacgagc gcaacccacg tccctagttg ccagcaattc agttgggaac   1080
tctatggaaa ctgccgatga taagtcggag gaaggtgtgg atgacgtcaa gtcctcatgg   1140
gccttacggg ttgggctaca cacgtgctac aatggtggtg acagtgggtt aatcccaaa    1200 agccatctca gttcggattg tcctctgcaa ctcgagggca tgaagttgga atcgctagta   1260
atcgcggaac agcatgccgc ggtgaatacg ttcccgggcc ttgtacacac cgcccgtcac   1320
accatgggag ttggttctac ccgacgacgn tgcgctaacc ttcgggggc aggcggccac    1380 ggtaggatca gcgactgggg tgaagtcgta acaaggtagc cgtagggaa cctgcggctg    1440 gatcacctcc tt                                                       1452
```